United States Patent [19]

Baum et al.

[11] 4,159,381

[45] Jun. 26, 1979

[54] 4-(p-FLUOROBENZOYL)-1-[3-(p-FLUOROBENZOYL)PROPYL]PIPERIDINE

[75] Inventors: Laszlo Baum, La Tour-de-Peilz; Philippe Pochon, Collonges, both of Switzerland

[73] Assignee: A. H. Robins Company, Inc., Richmond, Va.

[21] Appl. No.: 850,319

[22] Filed: Nov. 10, 1977

Related U.S. Application Data

[63] Continuation of Ser. No. 736,966, Oct. 29, 1976, abandoned.

[51] Int. Cl.² .................................... C07D 211/62
[52] U.S. Cl. ............................................ 546/245
[58] Field of Search ................................ 260/293.88

[56] References Cited

FOREIGN PATENT DOCUMENTS 1042294  9/1966  United Kingdom ............... 260/293.88

Primary Examiner—Norma S. Milestone

[57] ABSTRACT

A novel process for the preparation of 4-(p-fluorobenzoyl)-1-[3-(p-fluorobenzoyl)propyl]piperidine and the acid addition salts thereof is disclosed.

2 Claims, No Drawings

4-(P-FLUOROBENZOYL)-1-[3-(P-FLUOROBENZOYL)PROPYL]PIPERIDINE

This is a continuation, of application Ser. No. 736,966, filed Oct. 29, 1976 and now abandoned.

The present invention relates to 4-(p-fluorobenzyl)-1-[3-(p-fluorobenzyl)propyl]piperidine, its acid addition salts, and a novel procedure for the preparation thereof.

4-(p-Fluorobenzoyl)-1-[3-(p-fluorobenzoyl)propyl]piperidine and acid-addition salts thereof are disclosed in U.S. Pat. No. 3,576,810. The compound is prepared by the condensation of 4-(p-fluorobenzoyl)piperidine hydrochloride and 3-(p-fluorobenzoyl) propylchloride in a lower alkanol solvent in the presence of an alkali metal carbonate.

In the foregoing synthesis the 3-(p-fluorobenzyl)propyl chloride reactant is preferably employed in the form of its ketal, i.e., as 2-(p-fluorophenyl)-2-(3-chloropropyl)-1,3-dioxolane. The use of the ketal reactant results in increased yields of final product having a high degree of purity. The 2-(p-fluorophenyl)-2-[3-(p-fluorobenzoylpiperidino)propyl[-1,3-dioxolane thus obtained is treated with dilute mineral acid to regenerate the free carbonyl group.

The method referred to hereinabove requires the added steps of preparation of the ketal and the regeneration of the free ketone. We have now found that 4-(p-fluorobenzoyl)-1-[3-(p-fluorobenzoyl)propyl]piperidine hydrochloride can be prepared in good yield and in very pure form free of interfering by-products by converting N-γ-carboxypropylisonipecotic acid into the di-acid chloride and reacting the di-acid chloride with two moles of fluorobenzene. The hydrochloride salt of the desired product is obtained directly in substantially pure form and is readily purified by recrystallization.

It is therefore an object of the present invention to provide a novel process for the preparation of 4-(p-fluorobenzoyl)-1-[3-(p-fluorobenzoyl)propyl]piperidine hydrochloride. Another object is to provide a novel process for the preparation of 4-(p-fluorobenzoyl)-1-[3-(p-fluorobenzoyl)propyl]piperidine hydrochloride in good yield and in very pure form free of contaminating by-products. Additional objects will become apparent from the description which follows and the appended claims.

The following illustrates the novel process of the present invention.

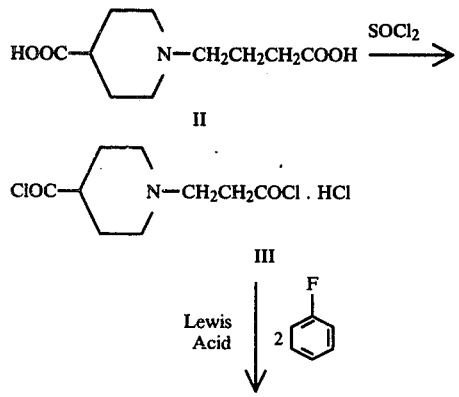

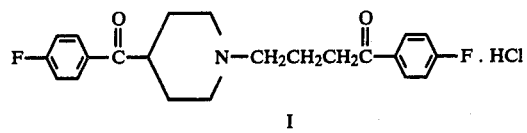

According to the novel process of the present invention, N-γ-carboxypropylisonipecotic acid II is converted into the di-acid chloride hydrochloride III by using a suitable chlorinating agent as, for example, thionyl chloride, phosphorous trichloride or phosphorous pentachloride. The reaction is carried out in a suitable inert solvent such as dichloromethane, trichloromethane, carbon tetrachloride, fluorobenzene, benzene, toluene or the like. Fluorobenzene represents a preferred solvent as the chlorination and the reaction of the di-acid chloride with fluorobenzene can be carried out as a single step without isolation of the di-acid chloride. The condensation of the di-acid chloride and fluorobenzene is carried out in the presence of a suitable Lewis acid, aluminum chloride being preferred, to give 4-(p-fluorobenzoyl)-1-[3-(p-fluorobenzoyl) propyl]piperidine hydrochloride I.

The foregoing general description is exemplified by the following preparation and examples which are not to be construed as limiting.

PREPARATION 1

Ethyl N-γ-carbethoxypropylisonipecotinate.

Ethyl isonipecotinate (125.77 g., 0.80 mole) is dissolved in 1,000 ml. of acetone, and 166.0 g. (1.2 mole) of potassium carbonate are added. Ethyl γ-bromobutyrate (171 g., 0.88 mole) is added dropwise with stirring at 20°–25° C. The mixture is heated for 24 hours at reflux (56°–60° C.). The mixture is cooled to 10°–15° C., the inorganic salts are removed by filtration, and the acetone filtrate is concentrated. The oily residue is distilled at 140°–142° C. (0.3 mm) to give 195–199 g. (90–92%) of a colorless oil.

Ethyl γ-chlorobutyrate can be used in the condensation giving the product in somewhat lower yield (54%).

EXAMPLE 1

N-γ-Carboxypropylisonipectic Acid Hydrochloride.

To a stirred mixture of 189.9 g. of ethyl N-γ-carbethoxypropylisonipecotinate and 300 ml. of water is added rapidly 200 ml. of concentrated hydrochloric acid. The temperature rises rapidly to 50° C. giving a clear solution. The mixture is refluxed for 3–4 hours, the temperature is lowered to about 45° C. and vacuum applied to remove as much water as possible. The pasty residue is treated with 350 ml. of isopropanol, cooled to 0°–5° C. and the crystalline product collected and washed with isopropanol. The dried colorless crystalline product (70°–80° C.) weighed 143-2 g. (81.47%) and melted at 202°–203° C.

N-γ-Carboxypropylisonipecotic acid hydrochloride is very soluble in water, slightly soluble in methanol and 95% ethanol and insoluble in absolute ethanol, isopropanol, chloroform and acetone.

EXAMPLE 2

4-(p-Fluorobenzoyl)-1-[3-(p-fluorobenzoyl)propyl]-piperidine Hydrochloride.

N-γ-Carboxypropylisonipecotic acid hydrochloride (50.3 g., 0.2 mole) is suspended in 250 ml. freshly distilled fluorobenzene, 1 ml. dimethylformamide (catalyst) is added, followed by the dropwise addition of 50 g. (0.42 mole) thionylchloride with stirring. Upon completion of the addition, the reaction mixture is heated cautiously to 50°–55° C. at which temperature vigorous formation of hydrochloric acid and sulfur dioxide commences. The temperature is maintained at 50°–55° C. until a clear reduction of the gas formation is observed, and then the mixture is heated slowly to reflux (78°–85° C.) at which temperature once again formation of gas commences. After heating at reflux for five hours, about 50 ml. of fluorobenzene are removed by distillation (in order to remove excess thionylchloride), and the dark colored mixture is cooled to 15° C. While the temperature is maintained below 30° C., 93.4 g. (0.7 mole) of anhydrous aluminum chloride are added in portions. The reaction between fluorobenzene and the di-acid chloride occurs with development of heat and hydrogen chloride. Stirring at a temperature below 30° C. is continued for some time, and the mixture is then heated slowly to reflux (80°–85° C.) and maintained at reflux for six hours. The reaction mixture is cooled to 10°–15° C. and poured with stirring onto 400 g. crushed ice. During this operation a temperature below 30° C. is maintained. From this mixture as much fluorobenzene as possible is removed by distillation under slight vacuum (70–90 mm) and a pot temperature of 35° C. (foaming) to facilitate filtration of the product. The mixture is cooled to 5° C., the precipitate is removed by filtration and mixed with 250 ml. acetone. The mixture is heated briefly (30 minutes) to reflux, then cooled to 5° C. and the precipitate is removed by filtration, washed with acetone, and dried in vacuo at 60° C. The dried tan colored product weighed 57 g. (70% yield).

The crude hydrochloride (48 g.) is dissolved in 960 ml. water heated to boiling, treated with activated charcoal and filtered while hot. The filter is rinsed with 75 ml. hot water. The filtrate is cooled to 0°–5° C. for five hours; the colorless crystals are removed by filtration, washed with cold water and dried in vacuo at 70° C. The dried white crystalline product weighed 35.8 g. (74.6%) and melted at 260° C. (dec.).

The free base 4-(p-fluorobenzoyl)-1-[3-(p-fluorobenzoyl) propyl]piperidine can be readily obtained by partition of the hydrochloride salt between chloroform and dilute aqueous base, separation and drying of the chloroform solution and concentration of the dried solution under reduced pressure. The free base thusly obtained can then be converted into any desired acid addition salt by reacting stoichiometric amounts of the free base and an inorganic or organic acid in a suitable lower alkanol solvent as, for example, ethanol or isopropanol and precipitating the acid addition salt thus formed by the addition of ether.

We claim:
1. Ethyl N-γ-carbethoxypropylisonipectinate.
2. N-γ-carboxypropylisonipecotic acid hydrochloride.

UNITED STATES PATENT AND TRADEMARK OFFICE
CERTIFICATE OF CORRECTION

PATENT NO. : 4,159,381
DATED : Jun. 26, 1979
INVENTOR(S) : Laszlo Baum and Philippe Pochon It is certified that error appears in the above-identified patent and that said Letters Patent are hereby corrected as shown below:

Column 1, lines 7 and 8, both instances, change "fluorobenzyl" to read --fluorobenzoyl--

Column 1, line 18, change "fluorobenzyl" to read --fluorobenzoyl--

Column 1, line 60, Formula III should appear as follows:

instead of as in the patent.

Column 2, line 47, change "carboxypropylisonipectic" to read --carboxypropylisonipecotic--

Column 4, line 28, change "carbethoxypropylisonipectinate" to read --carbethoxypropylisonipecotinate--

*Signed and Sealed this*

*Twenty-seventh* Day of *November 1979*

[SEAL]

Attest:

RUTH C. MASON
*Attesting Officer*

LUTRELLE F. PARKER
*Acting Commissioner of Patents and Trademarks*